(12) United States Patent
Thornton et al.

(10) Patent No.: US 11,534,329 B1
(45) Date of Patent: Dec. 27, 2022

(54) REUSABLE MENSTRUAL DISCHARGE COLLECTION DEVICE

(71) Applicant: Casco Bay Molding, Sanford, ME (US)

(72) Inventors: Elizabeth Thornton, Scarborough, ME (US); Andrew Powell, Somerville, MA (US)

(73) Assignee: Casco Bay Molding, Sanford, ME (US)

( * ) Notice: Subject to any disclaimer, the term of this patent is extended or adjusted under 35 U.S.C. 154(b) by 0 days.

(21) Appl. No.: 17/455,555

(22) Filed: Nov. 18, 2021

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC ........ A61F 5/451; A61F 5/455; A61F 5/4553; A61F 5/4404
See application file for complete search history.

(56) References Cited

U.S. PATENT DOCUMENTS

| | | | | | |
|---|---|---|---|---|---|
| 1,891,761 | A | * | 12/1932 | Goodard | A61F 5/4553 604/330 |
| 1,996,242 | A | * | 4/1935 | Hagedorn | A61F 5/4553 604/330 |
| 2,089,113 | A | * | 8/1937 | Chalmers | A61F 5/4553 D24/141 |
| 2,321,340 | A | * | 6/1943 | Waterbury | B29C 70/70 264/294 |
| 2,534,900 | A | * | 12/1950 | Chalmers | A61F 5/4553 604/330 |
| 2,616,426 | A | * | 11/1952 | Adele | A61F 5/4553 604/330 |
| 2,836,177 | A | * | 5/1958 | Sells | A61F 6/08 128/837 |
| 3,128,767 | A | * | 4/1964 | Nolan | A61F 6/08 604/330 |
| 3,404,682 | A | * | 10/1968 | Waldron | A61F 13/26 128/838 |
| 3,626,942 | A | * | 12/1971 | Waldron | A61F 6/08 604/330 |
| 3,841,333 | A | * | 10/1974 | Zalucki | A61F 5/4553 604/330 |
| 3,845,766 | A | * | 11/1974 | Zoller | A61F 5/4553 D24/141 |

(Continued)

*Primary Examiner* — Guy K Townsend
(74) *Attorney, Agent, or Firm* — ePatentManager.com; Guerry L. Grune

(57) ABSTRACT

A reusable menstrual discharge collection device is described comprising: a continuous single piece article that forms a menstrual discharge disc-shaped collection device with a half spherical dome catch where the half spherical dome catch includes a continuous top and bottom portion, and wherein the continuous top portion is attached to a continuous flexible hinge that is placed along an entire circumferential upper portion of the half spherical dome catch and wherein the hinge also forms a base for and is connected to a 360 degree continuous rim section such that the hinge allows the continuous rim section to be in both an inverted use position/configuration that allows movement of the rim section toward the half dome spherical catch allowing for adjustability to fit multiple cervix physiologies and the elongated configuration that allows for ease of manufacturing and cleaning.

15 Claims, 14 Drawing Sheets

(56) References Cited

U.S. PATENT DOCUMENTS

| Patent/Pub No. | | Date | Inventor | Class |
|---|---|---|---|---|
| 4,381,771 A | * | 5/1983 | Gabbay | A61F 6/08 128/836 |
| 4,799,929 A | * | 1/1989 | Knowles | A61F 5/4553 604/331 |
| 4,848,363 A | * | 7/1989 | Cattanach | A61F 5/4553 128/834 |
| 4,961,436 A | * | 10/1990 | Koch | A61F 6/08 128/834 |
| D323,212 S | * | 1/1992 | Crawford | D24/141 |
| 5,295,984 A | * | 3/1994 | Contente | A61F 5/4553 604/327 |
| 5,827,248 A | * | 10/1998 | Crawford | A61F 5/4553 604/328 |
| 5,928,249 A | * | 7/1999 | Saadat | A61B 17/42 606/119 |
| 5,947,992 A | * | 9/1999 | Zadini | A61F 5/4553 606/191 |
| 6,126,616 A | * | 10/2000 | Sanyal | A61B 10/0291 128/834 |
| 6,168,609 B1 | * | 1/2001 | Kamen | A61F 5/4553 600/573 |
| 6,241,846 B1 | * | 6/2001 | Contente | B29C 65/02 156/379 |
| 6,264,638 B1 | * | 7/2001 | Contente | A61M 31/002 604/285 |
| 6,332,878 B1 | * | 12/2001 | Wray | A61F 6/08 128/830 |
| 6,796,973 B1 | * | 9/2004 | Contente | A61F 5/4553 128/832 |
| 7,845,355 B2 | * | 12/2010 | Moench | A61F 6/08 128/833 |
| 8,454,493 B2 | * | 6/2013 | La Vean | A61F 6/08 600/33 |
| 8,690,847 B2 | * | 4/2014 | Norman | A61F 5/4553 604/327 |
| 8,795,248 B2 | * | 8/2014 | Shihata | A61F 5/4553 604/385.18 |
| 9,357,982 B2 | * | 6/2016 | Edmunds | A61F 13/2045 |
| 10,016,308 B2 | * | 7/2018 | Knox | A61F 13/00085 |
| D852,361 S | * | 6/2019 | Sedic | D24/141 |
| D852,362 S | * | 6/2019 | Sedic | D24/141 |
| 10,357,395 B2 | * | 7/2019 | Miller | A61F 5/4553 |
| D864,390 S | * | 10/2019 | Sedic | D24/141 |
| D892,324 S | * | 8/2020 | Yi | D24/141 |
| D894,386 S | * | 8/2020 | LeClerc | D24/141 |
| D895,798 S | * | 9/2020 | Newman | D24/141 |
| D895,799 S | * | 9/2020 | Newman | D24/141 |
| D895,800 S | * | 9/2020 | Knox | A61F 5/4404 D24/141 |
| 10,893,975 B2 | * | 1/2021 | Sedic | A61F 5/4553 |
| 10,959,873 B2 | * | 3/2021 | Wilson | A61F 5/4553 |
| 10,973,496 B2 | * | 4/2021 | Naseri | A61F 13/535 |
| D923,785 S | * | 6/2021 | Tsai | D24/141 |
| 2008/0077097 A1 | * | 3/2008 | Chambers | A61F 5/4553 604/330 |
| 2008/0200888 A1 | * | 8/2008 | Gooch | A61F 5/4553 604/330 |
| 2010/0242968 A1 | * | 9/2010 | Vean | A61F 6/08 128/830 |
| 2010/0312204 A1 | * | 12/2010 | Sheu | A61F 5/4408 604/330 |
| 2013/0110060 A1 | * | 5/2013 | Shihata | A61F 5/4553 604/330 |
| 2014/0012216 A1 | * | 1/2014 | Shaviv | A61F 5/4553 29/428 |
| 2015/0164680 A1 | * | 6/2015 | Chen | A61F 13/8405 604/359 |
| 2016/0278988 A1 | * | 9/2016 | Knox | A61F 15/005 |
| 2017/0189222 A1 | * | 7/2017 | Lin | A61F 5/4553 |
| 2017/0360594 A1 | * | 12/2017 | Park | A61F 5/449 |
| 2018/0028350 A1 | * | 2/2018 | Wilson | A61F 5/4553 |
| 2018/0199874 A1 | * | 7/2018 | Hwang | A61B 10/0045 |
| 2018/0214298 A1 | * | 8/2018 | Medas | A61F 5/4553 |
| 2019/0021898 A1 | * | 1/2019 | Ahn | A61F 5/4553 |
| 2019/0083296 A1 | * | 3/2019 | Miller | A61F 5/4404 |
| 2019/0099166 A1 | * | 4/2019 | Naseri | A61F 13/15 |
| 2019/0125571 A1 | * | 5/2019 | Hu | A61F 5/4553 |
| 2019/0282350 A1 | * | 9/2019 | Conti | A61B 10/0045 |
| 2019/0314191 A1 | * | 10/2019 | Bobarikin | A61F 5/4553 |
| 2019/0336318 A1 | * | 11/2019 | Kubo | A61F 5/455 |
| 2019/0358077 A1 | * | 11/2019 | Bauer | A61F 5/4553 |
| 2020/0022835 A1 | * | 1/2020 | Lloveras Maciá | A61F 5/4404 |
| 2020/0046572 A1 | * | 2/2020 | Hwang | A61F 5/4404 |
| 2020/0078208 A1 | * | 3/2020 | Stoebe-Latham | A61F 5/4553 |
| 2020/0078209 A1 | * | 3/2020 | Stoebe-Latham | A61F 13/55175 |
| 2020/0179157 A1 | * | 6/2020 | Pitacco | A61F 5/4553 |
| 2020/0214876 A1 | * | 7/2020 | Tsai | A61F 5/4553 |
| 2021/0113363 A1 | * | 4/2021 | Evans | A61F 5/4553 |
| 2021/0128342 A1 | * | 5/2021 | Miller | A61F 5/4553 |

\* cited by examiner

REUSABLE MENSTRUAL DISCHARGE COLLECTION DEVICE

FIELD OF INVENTION

The present disclosure describes a reusable menstrual disc-shaped device produced from a single contiguous mold thereby providing a single reusable menstruation disc-shaped device or "menstrual disc".

BACKGROUND

The present invention relates generally to feminine hygiene devices, and more particularly to a menstrual discharge collection device for collecting menstrual discharge.

From the time after World War I, when bandages were marketed as sanitary napkins, to the present, there have been essentially only two types of commercially available menstrual collection products: sanitary napkins and tampons. Sanitary napkins, including the newer pads and shields, have the disadvantages of bulk, odor and leakage. They also present disposal problems, and they are sometimes detectable to others. Their absorbent nature can also create problems of contamination and infection. Tampons are also disadvantageous. The basic design of the tampon does not stop leakage and the externally worn string can lead to contamination. Tampons have fibers which irritate the vaginal mucosa. Absorptive tampons can also contribute to serious infections.

Earlier art describes absorptive cup-shaped vaginal tampons. These devices are bulky and difficult to use and uncomfortable to wear, and would have the same dangers of infection presented by conventional absorptive tampons. Other internal menstrual discharge collection devices are worn in a lower region of the vaginal canal and generate suction, particularly during removal. These devices can cause irritation and pressure, and, in rare cases these devices need to be removed by a doctor.

Further devices have rims with springs embedded therein. Such springs make the devices unnecessarily complicated and expensive to manufacture. The exterior configurations of these devices may also cause irritation when worn internally. Accordingly, there is a need in the art for a menstrual discharge collection device that avoids the problems associated with napkins and tampons, and that is convenient, comfortable, reliable and economical.

As a result, this device would tend to twist upon compression, making insertion of the device difficult. All of the prior art systems would be difficult to insert and remove, uncomfortable to wear, unreliable, and/or uneconomical to manufacture and market.

Accordingly, there is a need in the art for an intravaginal substance delivery system that can be conveniently and reliably used, and that can be used without discomfort, particularly during menses.

SUMMARY

The present disclosure describes a single continuous menstruation disc-shaped device designed to collect menstrual fluid during a person's menstrual cycle. The reusable menstruation disc-shaped device is produced from a single contiguous mold thereby providing a single reusable menstruation disc-shaped device or "menstrual disc". The disc-shaped device includes a hinge-enabled invertible rim that when in the elongated position exposes finger loops or other gripping or positioning features allowing for proper cleaning of the menstruation disc-shaped device. In addition, once the menstruation disc-shaped device is inverted during use, it provides a configuration that allows the finger loops or other gripping or positioning features to remain in a "hidden" position thus allowing for both ease of insertion, proper placement, retrieval, and removal.

More specifically, the present disclosure provides for a reusable menstrual discharge collection device, comprising: a continuous single piece article that forms a disc-shaped menstrual discharge collection device with a half spherical dome catch such that the half spherical dome catch includes a continuous top and bottom portion, wherein the continuous top portion is attached to a continuous flexible hinge that is placed along an entire circumferential upper portion of the half spherical dome catch and wherein the hinge also forms a base for and is connected to a 360 degree continuous rim section such that the hinge allows the continuous rim section to be in an inverted use position that allows movement of the rim section toward the half dome spherical catch such that the menstrual discharge collection device provides adjustability and ease of extraction with a required flexibility so that the menstrual discharge collection device fits multiple cervix physiologies.

This reusable menstrual discharge collection device includes an elongated configuration that provides for both ease of manufacturing and for cleaning said menstrual discharge collection device after use.

Here the rim section also provides at least two finger loops that are attached to the rim section and wherein the finger loops are retractable in that the finger loops wrap into an underside of the continuous 360 degree rim when the menstrual discharge collection device is in an inverted shape before, during, and after utilization.

The device is a menstrual disc-shaped device that also functions as a shallow cup.

The device is formed as a single article in a single mold that processes injection molded high temperature resistant thermoplastic rubber.

The rim section of said discharge collection device has a Shore A hardness of at least 35 durometer.

The half spherical dome catch is collapsible so as to be enclosed within the rim section when the device is in a use position.

The reusable menstrual discharge collection device of wherein the rim section has rounded edges.

The half spherical dome catch is collapsible so that the half spherical dome catch is enclosed within the rim section during use, and wherein the device is folded into a teardrop-like position that provides greater ease of insertion than conventional menstrual discharge collection devices.

Here it is also possible to provide an absorbent and antimicrobial substance is infused into the half spherical dome catch and more precisely within a bottom portion of the half spherical dome catch, and wherein a distance between the bottom portion of the reservoir and the rim is no less than approximately thirty millimeters when the reservoir is in the device-shaped configuration.

In addition, the rim section is an elastomeric rim section that together with the half spherical dome catch defines a first generally circular configuration for creating a collection space for collecting menstrual discharge, the rim section being compressible from the first configuration to a second generally teardrop-shaped configuration for insertion of the menstrual discharge collection device into position for use, wherein diametrically opposed portions of the rim section are in contact with each other when the rim section is in the second configuration, and wherein the rim section is capable of self-restoring from the second configuration to the first configuration, and wherein the rim section has a height, and a thickness, and wherein the rim section is formed of a high temperature resistant injection molded thermoplastic rubber; and wherein the rim section is formed of liquid silicone rubber.

Often, the device is entirely formed with liquid silicone rubber.

In addition, there are methods of using the menstrual devices described above. One such method includes using a reusable menstrual discharge collection device, comprising:

providing a continuous single piece article that forms a disc-shaped device with a half spherical dome catch, the half spherical dome catch includes a continuous top and bottom portion, wherein the continuous top portion is attached to a continuous flexible hinge that is placed along an entire circumferential upper portion of the half spherical dome catch and wherein the hinge also forms a base for and is connected to a 360 degree continuous rim section such that the hinge allows the continuous rim section to be in an inverted use position that allows movement of the rim section toward the half dome spherical catch while providing movement and adjustability to fit multiple cervix configurations and an elongated configuration that allows ease of cleaning and manufacturing and;

wherein the user inserts their fingers while holding a folded teardrop-shaped configuration of the disc-shaped device into their vagina and continue insertion in order to allow pushing the device until the device reaches a fornix of the user and such that a part of the 360 degree continuous rim section of the device is reachable with the user's finger(s) thereby allowing for tucking the device under a pubic bone of the user.

Using this method it is possible to ensure that the menstrual disc shaped device is tucked under the pubic bone the device is in a proper preferred location.

In addition, the menstrual disc shaped device can be folded into a teardrop shape prior to insertion thereby providing a smallest possible shape for easier and more comfortable insertion than has previously been possible.

It is also an object of this disclosure to provide menstruation disc-shaped devices that are produced from a high temperature resistant thermoplastic elastomeric material, for example silicone rubber(s), fluorinated elastomers, and other high temperature resistant polymers capable of withstanding at least 100 C (for example, the boiling temperature of water). The polymer and/or polymer blend and/or polymer composite, must be able to withstand repeated thermal cycles of boiling liquids (most often water).

Menstrual disc-shaped devices can be created from any safe, acceptable elastomer. Platinum cured medical grade liquid silicone rubber is the preferred material.

In a further embodiment, additional alternative finger loop configurations are also provided. These finger loops can include a circumferential band or stem and loop design.

In another embodiment a polymer is provided (and often an elastomeric thermoset or thermoplastic polymer) that and can withstand at least one repeated usage of boiling water during the sanitization process and in this case the design will often function so that the product can provide at least 365 uses.

DETAILED DESCRIPTION

For the purpose of representing the principles of the disclosure and associated invention, reference will now be made to the drawings and specific language will be used to describe the same. It will nevertheless be understood that no limitation of the scope of the invention is thereby intended, such alterations and further modifications in the illustrated device and such further application of the principles of the invention as illustrated therein being contemplated as would normally occur to one skilled in the art are included as part of the present disclosure.

Figure 1:
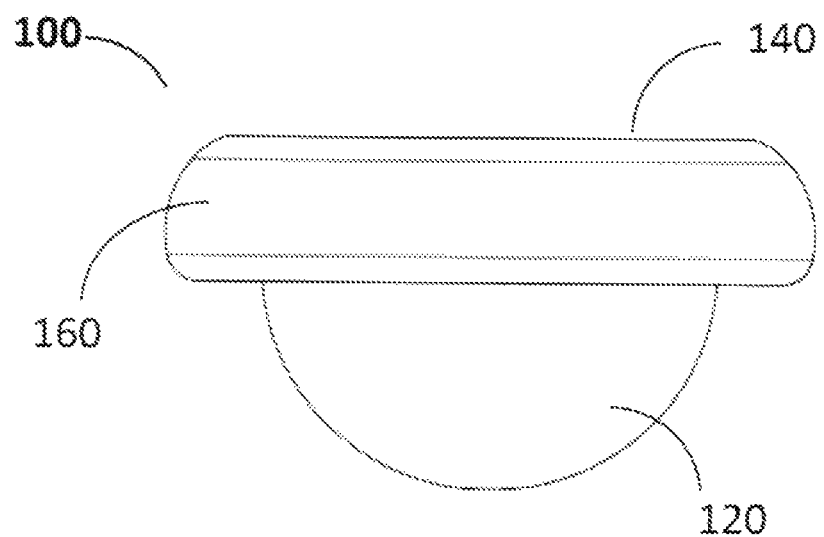
FIG. 1 shows the continuous, single piece article of a menstrual disc-shaped cup in the inverted use configuration.

FIG. 1 shows the continuous, single piece article of a menstrual disc-shaped device (100) in the inverted "use configuration" comprised of a generally half spherical, thin, flexible, dome shaped catch (120) section that leads to and includes the continuous flexible hinge (140) which facilitates the continuous 360 degree rim (160) shown in the menstrual disc-shaped device (100) use position encompassing the upper parts of the dome shaped catch (120) feature.

Figure 2:
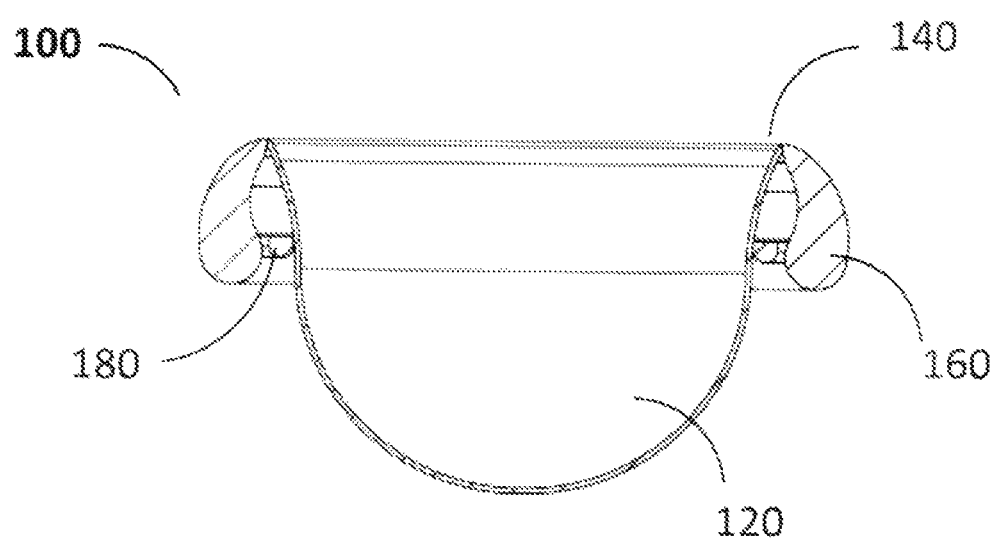
FIG. 2 provides a cross sectional cut view of the menstrual disc-shaped cup in its inverted use configuration.

FIG. 2 provides a cross sectional view of the menstrual disc-shaped device (100) also shown in its inverted "use configuration". This image more clearly illustrates how the 360 degree hinge (140) enables the rim (160) to invert back towards the dome shaped catch (120). Two of the finger loop (180) elements can be partially seen in this cross sectional view on the underside of the 360 degree rim (160) of the menstrual disc-shaped device (100) as shown.

Figure 3:
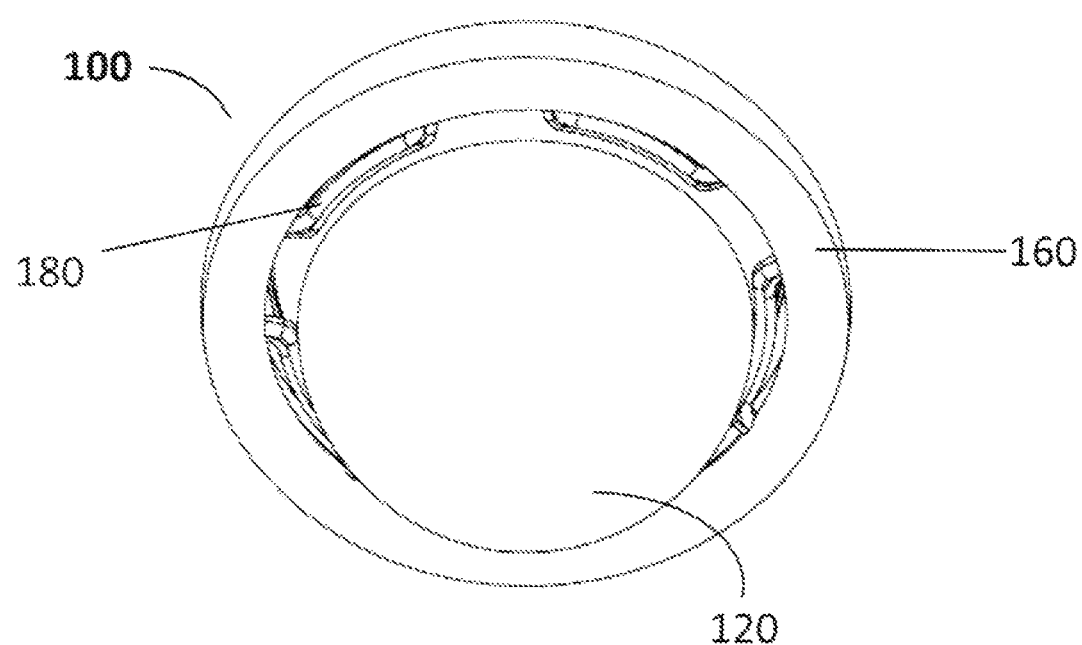
FIG. 3 illustrates the underside of the menstrual disc-shaped device in its inverted use position revealing a series of integrated attached loops.

FIG. 3 illustrates the underside of the menstrual disc-shaped device (100) in its inverted "use configuration" position revealing more clearly a series of integrated attached loops (180) that wrap the underside of the 360 degree rim (160) of the menstrual disc-shaped device (100).

Figure 4:
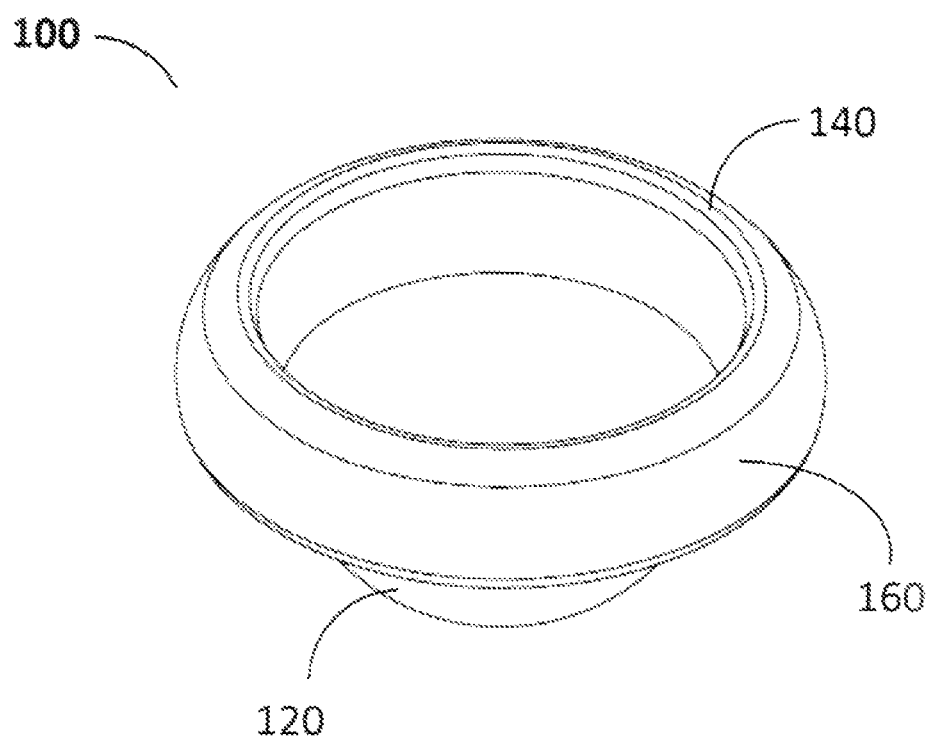
FIG. 4 offers an isometric top view of the menstrual disc-shaped device in its inverted use position revealing a top view of the continuous 360 degree hinge and 360 degree rim.

FIG. 4 offers an isometric top view of the menstrual disc-shaped device (100) in its inverted "use configuration" position more clearly revealing a top view of the continuous 360 degree hinge (140) and 360 degree rim (160). The finger loop (180) elements are concealed on the underside of the 360 degree rim (160) in the menstrual disc-shaped device (100).

Figure 5:
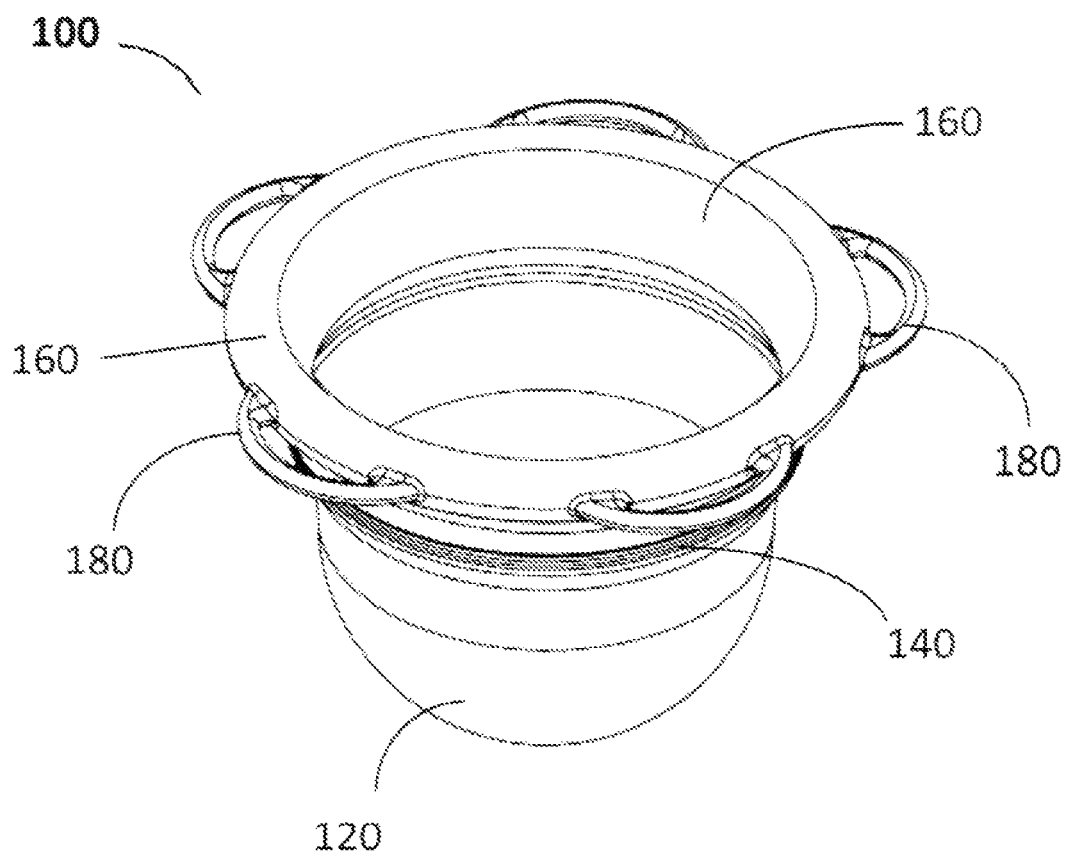
FIG. 5 is an isometric view of the menstrual disc-shaped device in its extended or elongated configuration.

FIG. 5 is an isometric view of the menstrual disc-shaped device (100) in an elongated configuration. This elongated configuration is optimal for cleaning and manufacturing of the menstrual disc-shaped device (100). The finger loops (180) are formed and attached to the outside of the 360 degree rim (160). The domed shaped catch (120) is attached as a single article to the continuous flexible integrated hinge (140) which is attached as a portion of and transitions to the 360 degree rim (160) that connects to the series of finger loops (180) so that all four major elements (120, 140,160, and 180) comprise a single menstrual disc-shaped device (100) device.

Figure 6:
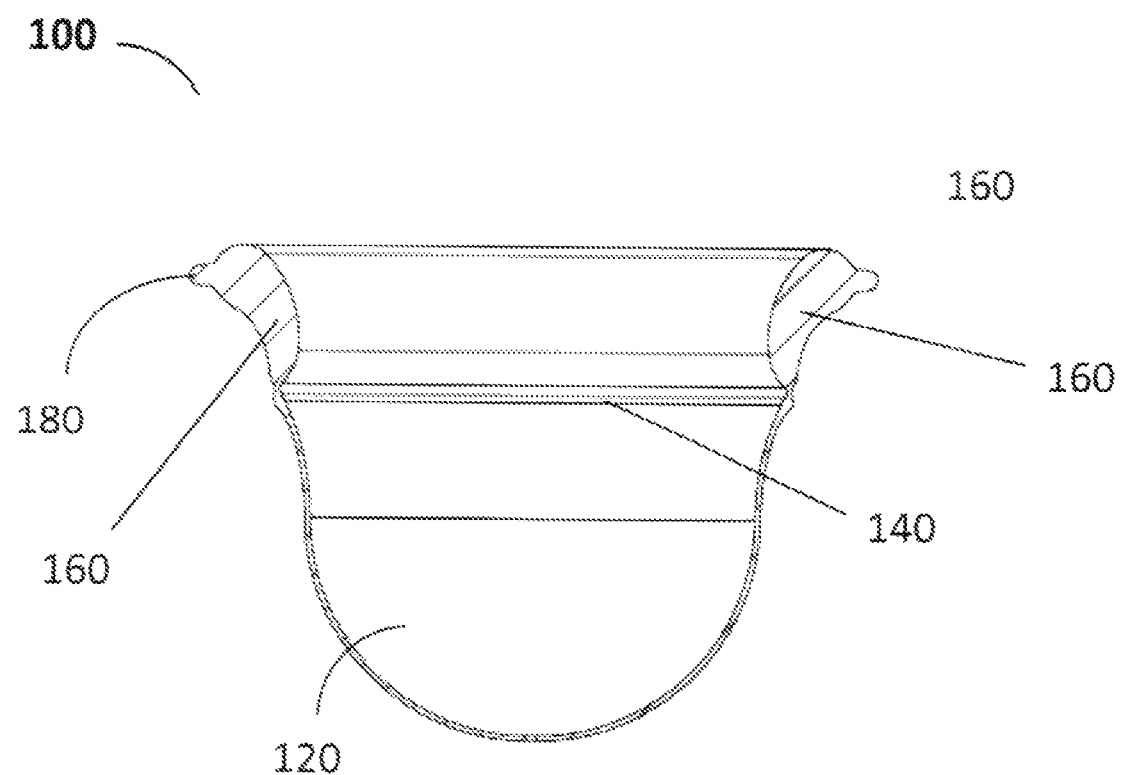
FIG. 6 offers a cross sectional cut view of the menstrual disc-shaped device in its elongated configuration.

FIG. 6 offers a cross sectional view of the menstrual disc-shaped device (100) in its elongated configuration. The thin flexible dome shape catch (120) is contiguous with and leads toward the 360 degree flexible hinge (140) which connects to the much thicker 360 degree rim (160). The thicker 360 degree rim (160) provides for and leads to the positioning of the multiple finger loops (180) which completes this version of the menstrual disc-shaped device (100) in its elongated configuration.

Figure 7:
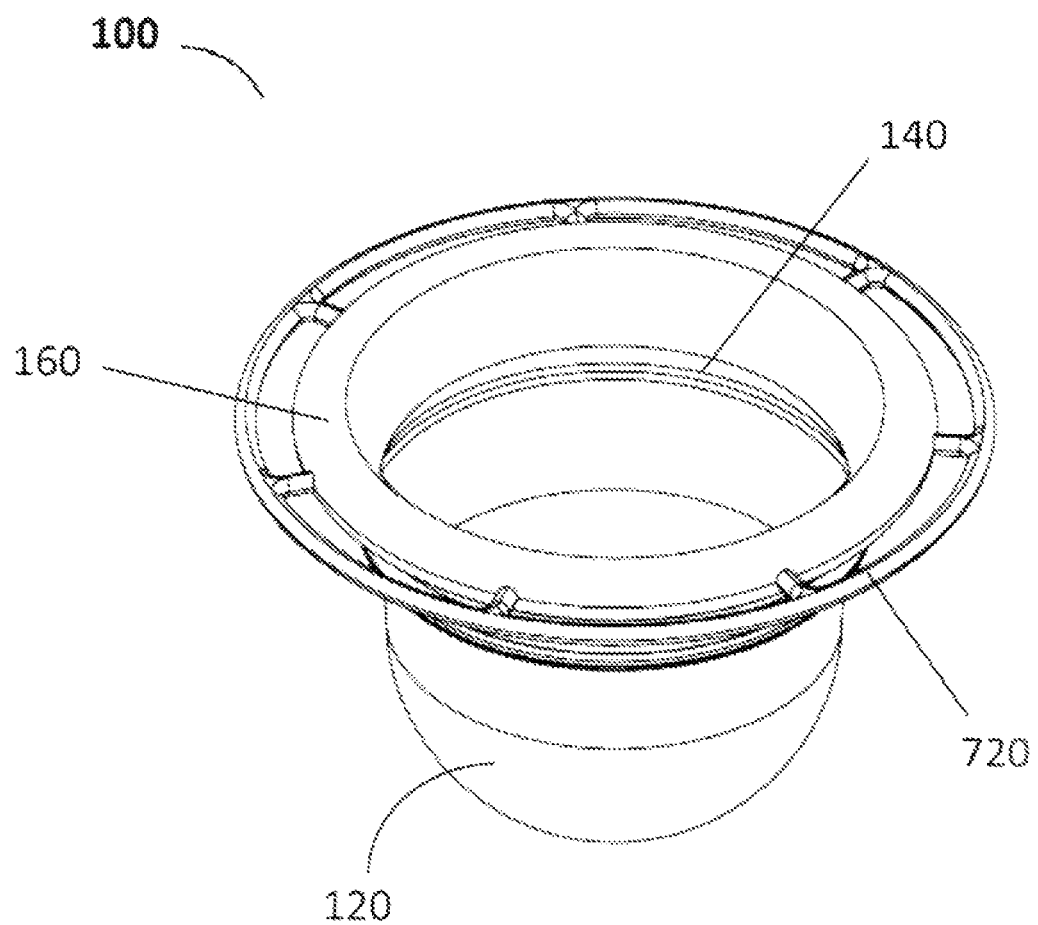
FIG. 7 depicts the menstrual disc-shaped device in its elongated configuration depicting an alternative circumferential finger loop element.

FIG. 7 depicts the menstrual disc-shaped device (100) in its elongated configuration with the domed shaped catch (120) attached to the continuous flexible integrated hinge (140) which provides for and transitions to the 360 degree rim (160). Here, the 360 degree rim (160), connects to an alternative circumferential finger loop element (720). The circumferential finger loop element (720) wraps around to the underside of the rim (160) when the menstrual disc-shaped device is placed in its inverted use condition. These same four major elements (120, 140,160, and 180) comprise a single menstrual disc-shaped device (100) device.

Figure 8:
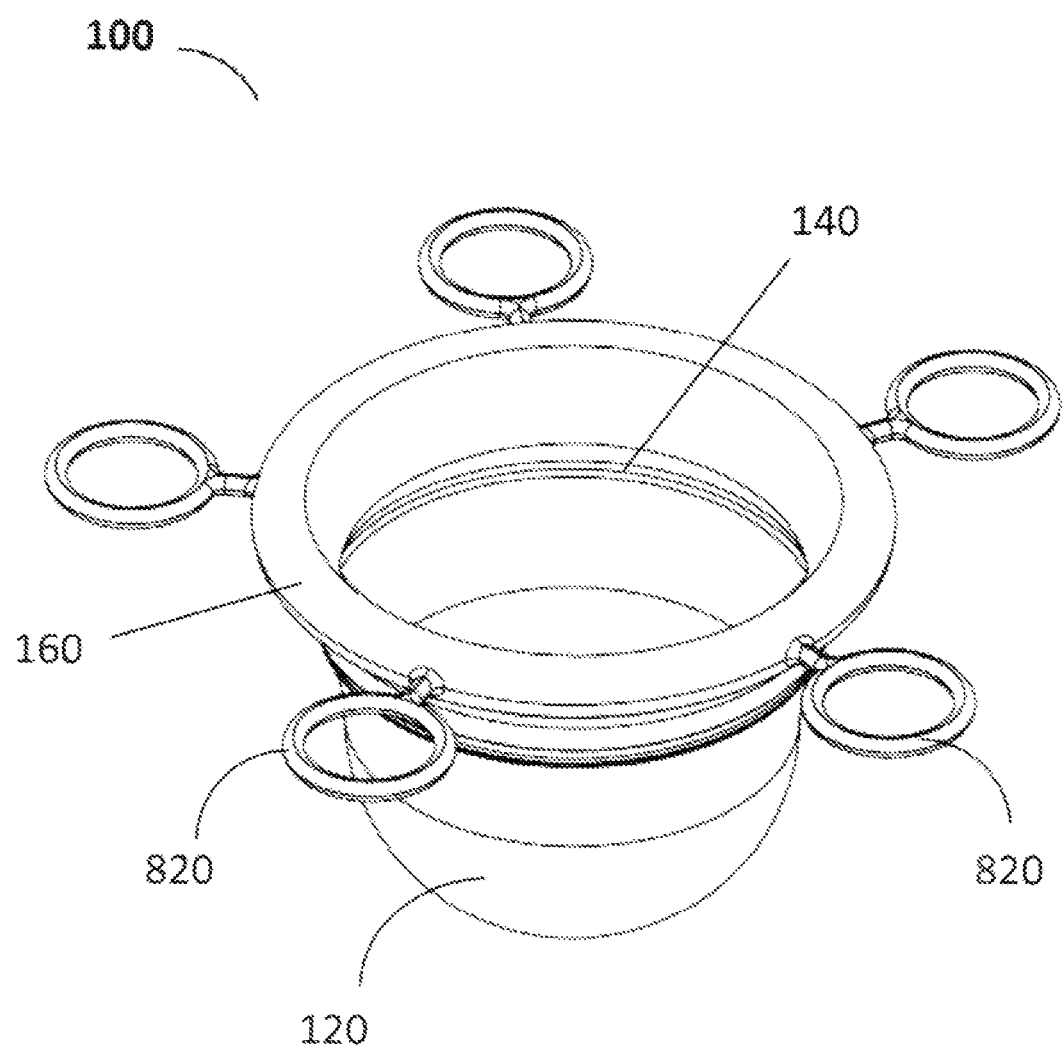
FIG. 8 depicts the menstrual disc-shaped device in its elongated configuration depicting an alternative stem and ring loop

FIG. 8 depicts the menstrual disc-shaped device (100) in its elongated configuration with the domed shaped catch (120) attached to the continuous flexible integrated hinge (140) which transitions to the 360 degree rim (160) that connects to an alternative stem and ring loop element (820). The stem and ring loop element (820) wraps to the underside of the 360 degree rim (160) when the menstrual disc-shaped device is placed in its inverted "use condition". All four major elements (120, 140,160, and 180) still comprise a single menstrual disc-shaped device (100) device.

Figure 9:
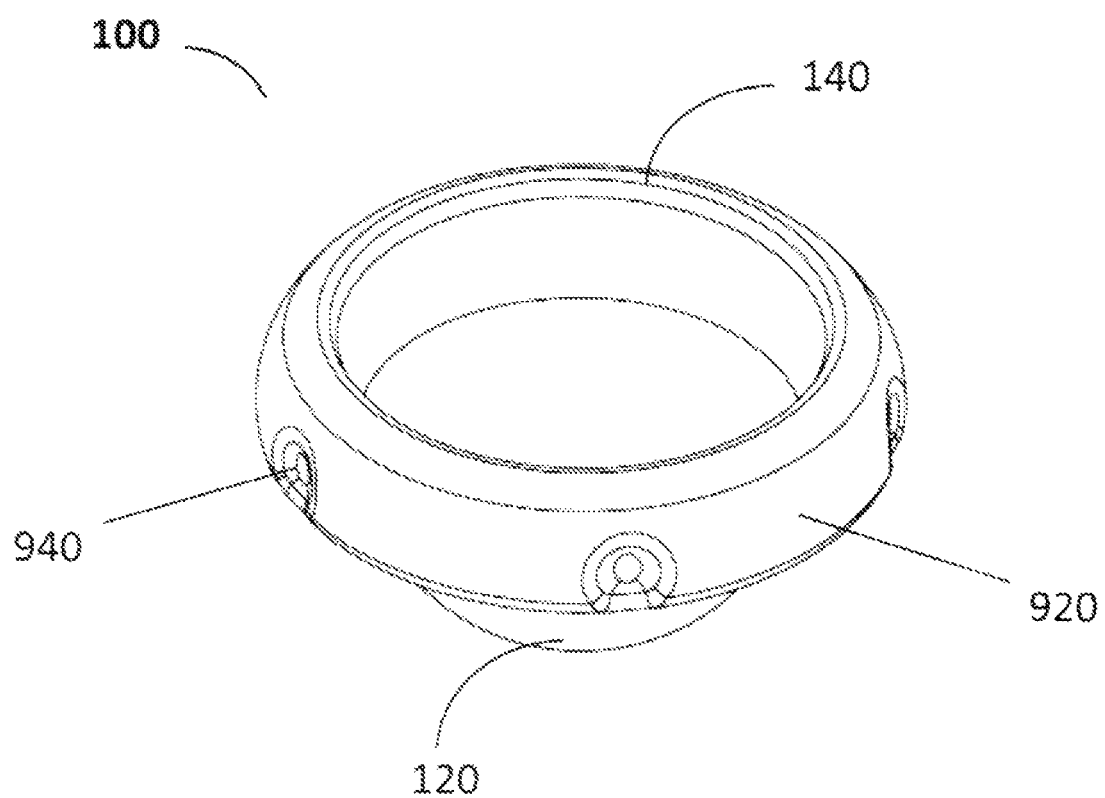
FIG. 9 illustrates an isometric view of a menstrual disc-shaped device in its inverted use configuration having a rim interrupted by gripping indentations or protrusions.

FIG. 9 illustrates an isometric view of a menstrual disc-shaped device (100) in its inverted use configuration with the domed shaped catch (120) attached to the continuous flexible integrated hinge (140) which transitions to an alternate 360 degree rim (920) interrupted by gripping indentations (940) so that any gripper protrusions are imbedded in order to remain flush along any surface of the alternate 360 degree rim (920) geometry.

Figure 10:
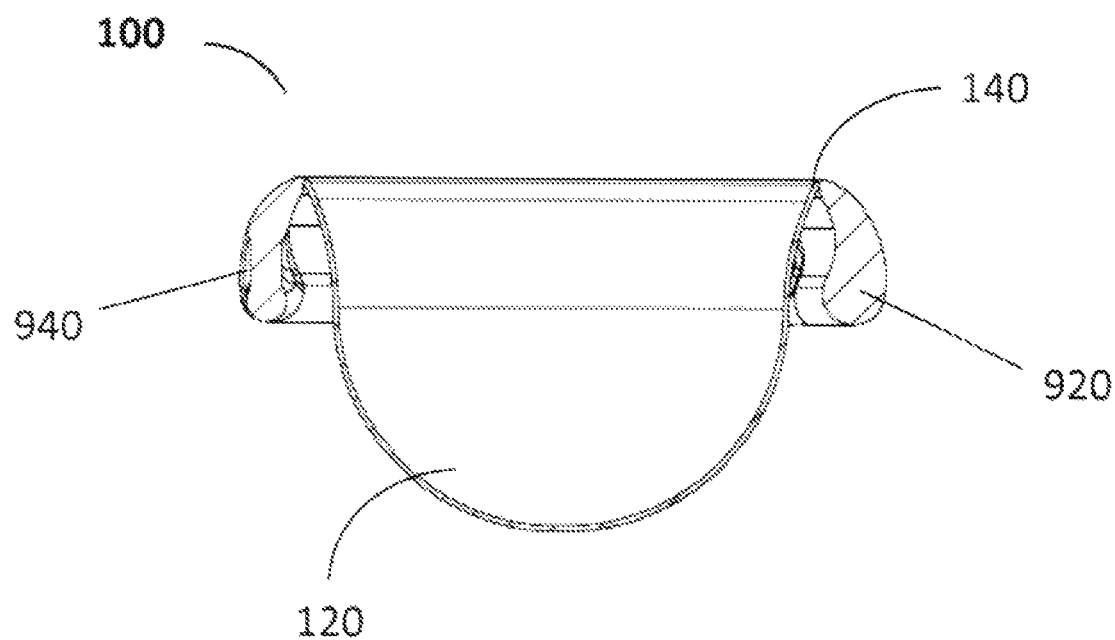
FIG. 10 offers a cross sectional cut view of the menstrual disc-shaped device in its inverted use configuration where the rim is interrupted by gripping indentations or protrusions.

FIG. 10 offers a cross sectional view of the same menstrual disc-shaped device (100) shown in FIG. 9 here in its inverted "use configuration" with the domed shaped catch (120) attached to the continuous flexible integrated hinge (140) which transitions to an alternate 360 degree rim (920) is interrupted by gripping indentations (940) or protrusions within the alternate geometry 360 degree rim (920) geometry.

Figure 11:
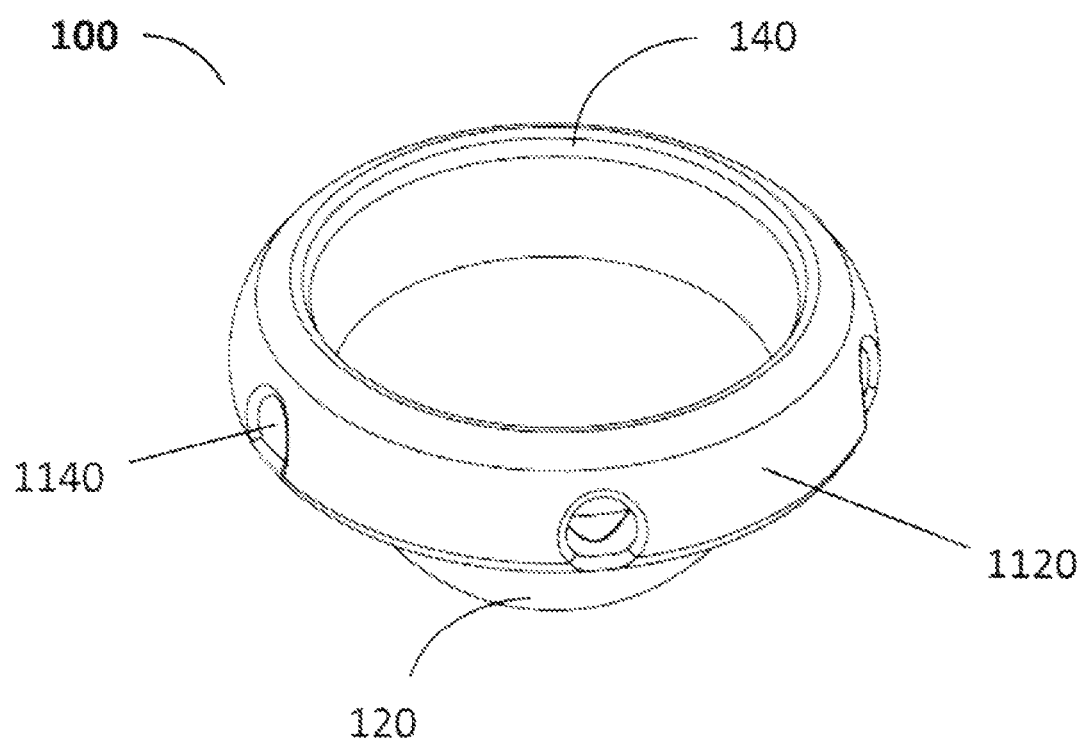
FIG. 11 illustrates an isometric view of a menstrual disc-shaped device in its inverted use configuration where the rim is interrupted by gripping through holes or protrusions.

FIG. 11 illustrates an isometric view of a menstrual disc-shaped device (100) in its inverted use configuration with the domed shaped catch (120) attached to the continuous flexible integrated hinge (140) that allows for transitioning to an alternate 360 degree rim (1120) interrupted by gripping through holes (1140) so that any gripper protrusions (1140) are imbedded in order to remain flush along any surface of the alternate 360 degree rim (1120) geometry.

Figure 12:
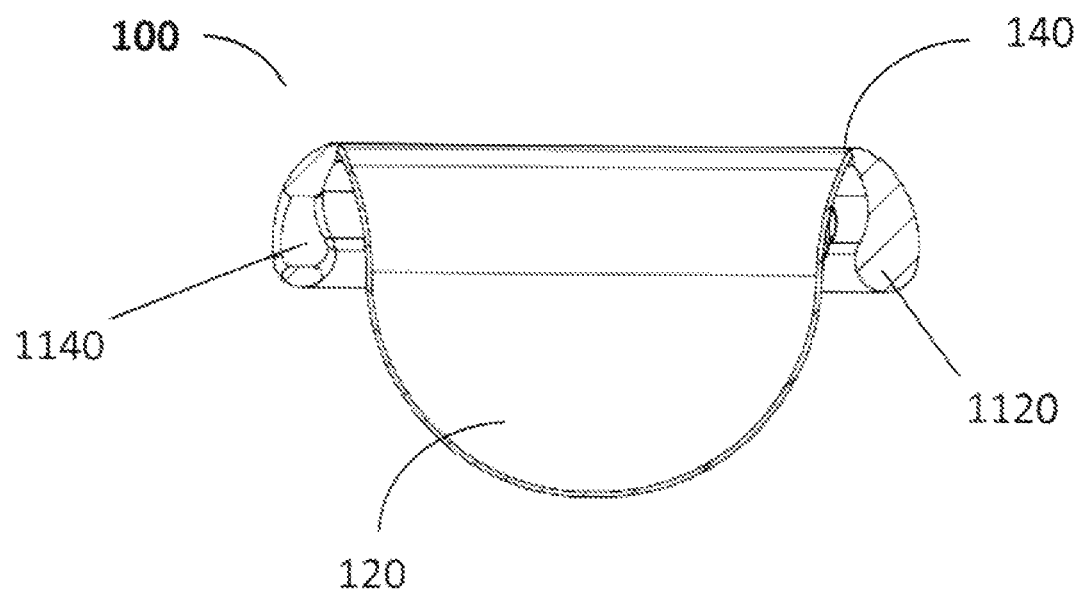
FIG. 12 offers a cross sectional cut view of the menstrual disc-shaped device in its inverted use configuration where the rim is interrupted by gripping through holes or protrusions.

FIG. 12 offers a cross sectional view of the menstrual disc-shaped device (100) in its inverted "use configuration" with the domed shaped catch (120) attached to the continuous flexible integrated hinge (140) that transitions to an alternate 360 degree rim (1120) interrupted by gripping through holes (1140) so that any gripper protrusions (1140) are imbedded in order to remain flush along any surface of the alternate 360 degree rim (1120) geometry The disc-shaped menstrual up device comprises at least four (4) major features offered in one complete, continuous menstruation disc-shaped device. These at least four features include; a catch, hinge, a rim, and finger loop(s). These four featured elements are further described below:

1) The catch provided is a thin-walled, flexible, pliable section of the device that provides a comfortable, dome-shaped element which functions as a device to catch and store menstrual fluid.

2) The hinge connects with the catch to provide a "built-in" living hinge arrangement which is a portion of the hinge that connects the thin flexible catch to an inverted rim. The hinge provides an ability to manufacture the rim such that elongation of the menstrual disc design and applied configuration eliminates the possibility of troublesome undercuts to facilitate ease of manufacturing.

The elongated configuration of the menstrual disc-shaped device also provides for finger loops to be easily added to the mold cavity and still allow a simple and reproducible manufacturing process resulting in the final product. The "living" hinge enables the rim to be inverted into a more conventional "use" or "usable" configuration. As the menstrual disc-shaped device is placed in an "inverted rim" or "in use configuration" or position, the menstrual disc-shaped device can be effectively positioned over the cervix. This "living" hinge also allows the user/menstruator to flip the rim back up, into the elongated configuration, for ease of cleaning, after removal and draining. This hinge feature enables the user to easily clean the menstrual disc-shaped device by allowing for exposure of all surfaces to running water and/or boiling water during washing cycles to assure proper sanitation. These washing cycles can be performed automatically in an automatic dishwasher.

3) The rim is optimized in order to provide the radial tear and tensile strength necessary so that the device can open easily and safely once the device is located beneath the cervix. The rim is designed to provide the necessary flexibility by ensuring proper flexural strength so that the device can be pinched by the user into a teardrop shape for easy vaginal insertion and location. This procedure is known as "folding". The 360-degree rim and associated geometry offers a major advantage over conventional designs for ease of removal. Other menstrual disc-shaped devices rotate while in use. The menstrual disc-shaped device without a complete 360 degree rim and multiple pull loop locations can be difficult to grip and extract.

The "use configuration" provides a menstruation disc-shaped device that includes the rim in a "flipped" or inverted position that is directed toward the catch, allowing the menstrual disc-shaped device to be inserted for use.

When the menstrual disc-shaped device is shown in FIG. 5 in its elongated configuration the rimmed portion includes attached multiple finger loops on the outside portion of the rim. The menstrual disc-shaped device as provided and shown in a cross sectional view in FIG. 2 in its use or inverted rim configuration, the attached multiple finger loops can be wrapped or otherwise folded toward the underside of the rim. The loops further aid the menstrual disc-shaped device user in locating and removing the menstrual disc.

In an additional embodiment, alternate configurations of the rim can be manufactured to provide indentions, protrusions and/or "through-orifices" in order to allow the user to more easily grip the disc-shaped device for insertion, repositioning, or removal. Inverting the rim configures the disc to provide a flexible, softer part of the disc so that the disc can be positioned in a more proximate location to the cervical area.

4) Multiple finger loops can be finger loops that are integrated into the rim geometry so that when the menstrual disc-shaped device is in the inverted use condition these further enhance the user/menstruator's ability to grip the rim by hooking their finger in a finger loop for easier removal even if the menstrual disc-shaped device has rotated. During use the finger loops are recessed and flush with the surfaces of the disc-shaped device. Previous designs provided the tethers attached on the outside of the rim, which greatly increased the chance of the tether irritating the menstruator.

Menstruators are people that come in all shapes and sizes, with different cervix heights and preferred menstrual device or disc-like geometries. The menstrual disc-shaped device described herein can be modified for different diameters and catch configurations to meet the needs for different users.

The most common method of manufacturing the menstrual disc-shaped device is by injection, transfer, or compression molding which enables the menstrual disc-shaped device be molded in an elongated "wind-sock" shaped design followed by removal and subsequent inversion to create the final rim detail.

Thermoplastics and Liquid Silicone Rubber (LSR) plastics are either organic or semi-organic (if inorganic fillers or inorganic monomers and polymers are used) materials that have (as their main attribute) relatively high tensile strength, elongation at break and tear strength due to their high molecular weights. Most engineers and manufacturers consider LSR's as thermosets in that they normally cannot be reused to make the same product. Alternatively, thermoplastics often allow the use of regrind during molding and extrusion operations. For the present disclosure the menstrual disc-shaped device is produced using one or more polymers that may include any of moldable thermosets, thermoplastics and/or elastomers. The list of possibilities includes thousands of variations of these polymers which includes polymer blends, composites, dual layered polymer systems, and also a large number of possible fillers to complete the product.

Smooth surfaces and transitions of the menstrual disc-shaped device are required to minimize the potential for irritation, facilitate cleaning, and ease of manufacturability.

The boiling water can be heated with one or more heating devices selected from the group consisting of ovens, stovetops, microwaves, wood-burning or other energy sourced stoves, infrared burners, sonic containers, and solar devices. In some cases, dishwashers and/or autoclaves can be used for cleaning and sanitizing purposes.

Working Example

Figure 13:
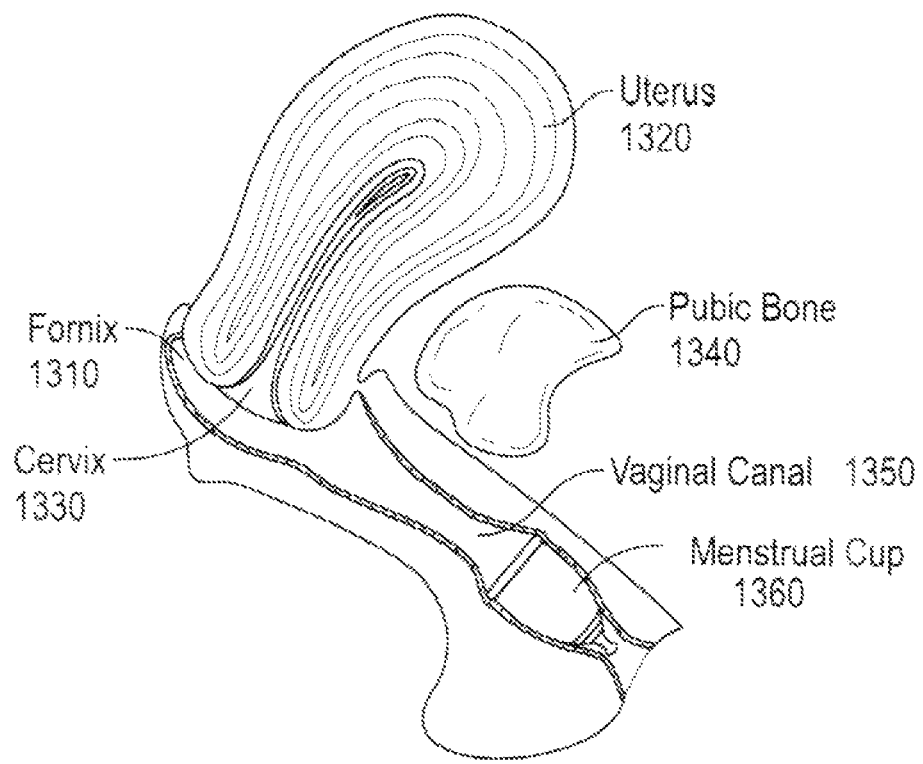
FIG. 13 provides a cross-sectional view of the location and position of the menstrual cup shaped device in the uterine canal to show the difference between cup and disc locations.
Figure 14:
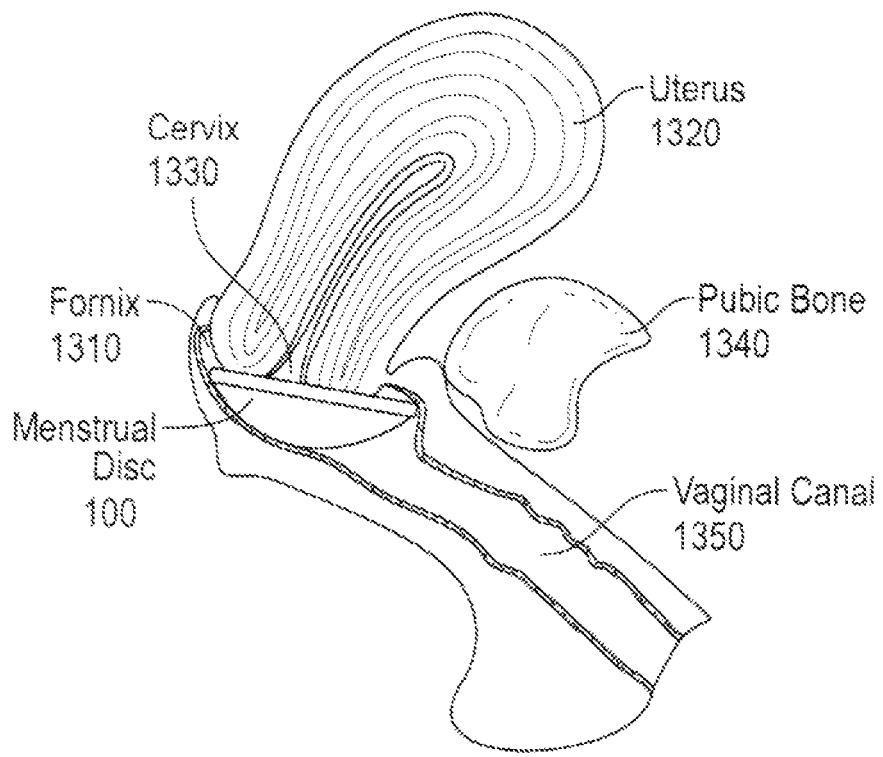
FIG. 14 illustrates a cross-sectional view of the position of the menstrual disc as it relates to the cervix and fornix to show the difference between cup and disc locations.

FIGS. 13 and 14 demonstrate how the devices of the present disclosure are utilized in practice. FIG. 13 shows that both the menstrual cup (1360) and menstrual disc (100) collect menstrual fluids and can be worn for up to 12 hours, however their location and use varies slightly.

As shown in FIG. 13, the menstrual cup (1360) is located/placed lower in the vaginal canal (1350) usually within an inch of the opening of the vagina. It uses the muscular structure of the vaginal walls to create a seal and prevent leaks.

FIG. 14 reveals the menstrual disc (100) positioned higher up in the vaginal canal (1350) in the fornix (1310), and sits directly below the cervix (1330). The menstrual disc (100) is tucked behind the pubic bone (1340) and uses the vaginal walls in the fornix (1310) to create a seal. The menstrual disc (100) differs from the menstrual cup (1360) in that the user can use the menstrual disc (100) during sexual intercourse.

Figure 15:
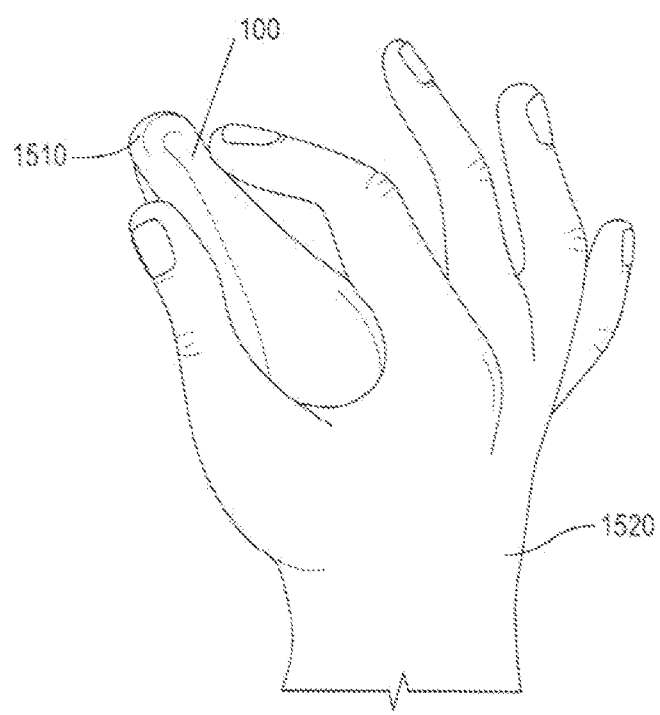
FIG. 15 illustrates one method of holding the menstrual disc shaped device folded in a teardrop shape prior to insertion.
Figure 16:
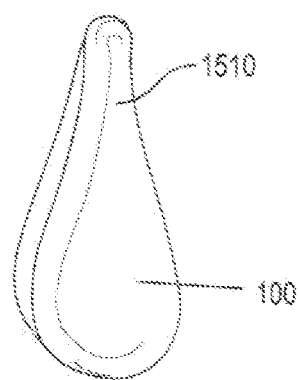
FIG. 16 illustrates the tear drop shape of the menstrual disc shaped device.

As stated above, FIG. 15 illustrates one method of holding the menstrual disc shaped device folded in a teardrop shape prior to insertion, while FIG. 16 illustrates the tear drop shape of the menstrual disc shaped device.

FIG. 15 shows how the menstrual disc will be held in the hand (1520) while folded in the teardrop shape (1510). Here the menstrual disc (100) is in the "pinched configuration". The user would then insert their fingers with the folded pinched configuration disc (1510) into their vagina and continue to push it in as far as possible until it reaches the fornix (1310) of FIG. 13 and FIG. 14 and opens. The part of the rim that the user can reach with their finger gets tucked under the pubic bone (1340) of FIG. 13 and FIG. 14. Once the menstrual disc (100) of FIG. 13 and FIG. 14 is tucked under the pubic bone (1340), it is in the proper preferred location.

FIG. 16 indicates what and how the menstrual discs (100) are folded into the teardrop shape (1510) prior to insertion. The pinched top of the menstrual discs (100) are folded and pinched into a teardrop shape (1510) that provides for the menstrual disc (100) to achieve the smallest possible shape for easier and more comfortable insertion than has previously been possible. The teardrop shape for the menstrual discs folded in teardrop shape (1510) as shown differs from other figure-8 shaped alternate possible shapes that created much larger, more uncomfortable, and sometimes impossible shapes that could be used for insertion into the vaginal canal.

What is claimed is:
1. A reusable menstrual discharge collection device, comprising:
a continuous single piece article that forms a disc-shaped menstrual discharge collection device with a half spherical dome catch such that said half spherical dome catch includes a continuous top and bottom portion, wherein said continuous top portion is attached to a continuous flexible integrated hinge that is placed along an entire circumferential upper portion of said half spherical dome catch and wherein said hinge also forms a base for and is connected to a 360 degree continuous rim section such that said hinge allows said continuous rim section to be in an inverted use position that allows movement of said rim section toward said half dome spherical catch that is also in an inverted position such that said menstrual discharge collection device provides adjustability and ease of extraction with a required flexibility so that said menstrual discharge collection device fits multiple cervix physiologies and said inverted catch allows for capture of said menstrual discharge.

2. The reusable menstrual discharge collection device of claim 1, wherein said device includes an elongated configuration that provides for both ease of manufacturing and for cleaning said menstrual discharge collection device after use.

3. The reusable menstrual discharge collection device of claim 1, wherein said device is a menstrual disc-shaped device that functions as a shallow cup.

4. The reusable menstrual discharge collection device of claim 1, wherein said device is formed as a single article in a single mold that processes injection molded high temperature resistant thermoplastic rubber.

5. The reusable menstrual discharge collection device of claim 3, wherein said rim section of said discharge collection device has a Shore A hardness of at least 35.

6. The reusable menstrual discharge collection device of claim 1, wherein said half spherical dome catch is collapsible so as to be enclosed within said rim section when said device is in a use position.

7. The reusable menstrual discharge collection device of claim 1, wherein said rim section has rounded edges.

8. The reusable menstrual discharge collection device of claim 1, wherein said half spherical dome catch is collapsible so that said half spherical dome catch is enclosed within said rim section during use, and wherein said menstrual discharge device is foldable into a tear drop-like position that provides greater ease of insertion than conventional menstrual discharge collection devices.

9. The reusable menstrual discharge collection device of claim 8, wherein an absorbent and antimicrobial substance is infused into said half spherical dome catch and more precisely within a bottom portion of said half spherical dome catch, and wherein a distance between said bottom portion of said reservoir and said rim is no less than approximately thirty millimeters when said reservoir is in said device-shaped configuration.

10. The reusable menstrual discharge collection device of claim 9, wherein a pharmaceutical or other medically active substance is infused into said half spherical dome catch and more precisely within a bottom portion of said half spherical dome catch, and wherein a distance between said bottom portion of said reservoir and said rim is no less than approximately thirty millimeters when said reservoir is in said device-shaped configuration.

11. The reusable menstrual discharge collection device of claim 1, wherein said rim section is an elastomeric rim section that together with said half spherical dome catch defines a first generally circular configuration for creating a collection space for collecting menstrual discharge, said rim section being compressible from said first configuration to a second generally tear drop-shaped configuration for insertion of said menstrual discharge collection device into position for use, wherein diametrically opposed portions of said rim section are in contact with each other when said rim section is in said second configuration, and wherein said rim section is capable of self-restoring from said second configuration to said first configuration, and wherein said rim section has a height, and a thickness, and wherein said rim section is formed of a high temperature resistant injection molded thermoplastic rubber; and wherein said rim section is formed of liquid silicone rubber.

12. The reusable menstrual discharge collection device of claim 11, wherein said device is entirely formed with liquid silicone rubber.

13. A method of using a reusable menstrual discharge collection device, comprising:
providing a continuous single piece article that forms a disc-shaped device with a half spherical dome catch, said half spherical dome catch includes a continuous top and bottom portion, wherein said continuous top portion is attached to a continuous flexible integrated hinge that is placed along an entire circumferential upper portion of said half spherical dome catch and wherein said hinge also forms a base for and is connected to a 360 degree continuous rim section such that said hinge allows said continuous rim section to be in an inverted use position that allows movement of said rim section toward said half dome spherical catch that is also in an inverted position while providing movement and adjustability to fit multiple cervix configurations and an elongated configuration that allows ease of cleaning and manufacturing and said inverted catch allows for capture of said menstrual discharge;
wherein said user inserts their fingers while holding a folded teardrop-shaped configuration of said disc-shaped device into their vagina and continue insertion in order to allow pushing said device until said device reaches a fornix of said user and such that a part of said 360 degree continuous rim section of said device is reachable with said user's finger(s) thereby allowing for tucking said device under a pubic bone of said user.

14. The method of claim 13, wherein once said menstrual discharge collection disc shaped device is tucked under said pubic bone said device is in a proper preferred location.

15. The method of claim 13, wherein said menstrual discharge collection disc shaped device is folded into a teardrop shape prior to insertion thereby providing a smallest possible shape for easier and more comfortable insertion than previous menstrual devices.

* * * * *